(12) United States Patent
Kim et al.

(10) Patent No.: US 8,992,519 B2
(45) Date of Patent: Mar. 31, 2015

(54) INVERTED BALLOON RF ABLATION CATHETER AND METHOD

(75) Inventors: Isaac Kim, San Jose, CA (US); Josef Koblish, Sunnyvale, CA (US); Robert F. Bencini, Sunnyvale, CA (US)

(73) Assignee: Boston Scientific Scime, Inc., Maple Grove, MN (US)

(*) Notice: Subject to any disclaimer, the term of this patent is extended or adjusted under 35 U.S.C. 154(b) by 739 days.

(21) Appl. No.: 13/295,438

(22) Filed: Nov. 14, 2011

(65) Prior Publication Data

US 2012/0130363 A1    May 24, 2012

Related U.S. Application Data

(60) Provisional application No. 61/416,597, filed on Nov. 23, 2010.

(51) Int. Cl.
  *A61B 18/18*  (2006.01)
  *A61B 18/14*  (2006.01)
  *A61B 18/00*  (2006.01)

(52) U.S. Cl.
  CPC ... *A61B 18/1492* (2013.01); *A61B 2018/00238* (2013.01); *A61B 2018/00375* (2013.01); *A61B 2018/00839* (2013.01)
  USPC .............................................. 606/41; 606/33

(58) Field of Classification Search
  CPC ........... A61B 2018/00214–2018/00232; A61B 18/1492; A61F 7/123; A61F 7/12
  USPC ................. 606/41, 33; 607/101, 102
  See application file for complete search history.

(56) References Cited

U.S. PATENT DOCUMENTS

| | | | |
|---|---|---|---|
| 5,991,650 A | 11/1999 | Swanson et al. |
| 6,097,976 A | 8/2000 | Yang et al. |
| 6,256,525 B1 | 7/2001 | Yang et al. |
| 6,357,447 B1 | 3/2002 | Swanson et al. |
| 6,464,700 B1 | 10/2002 | Koblish et al. |
| 6,468,272 B1 | 10/2002 | Koblish et al. |
| 6,542,781 B1 | 4/2003 | Koblish et al. |
| 6,610,055 B1 | 8/2003 | Swanson et al. |
| 6,613,046 B1 | 9/2003 | Jenkins et al. |
| 6,645,200 B1 | 11/2003 | Koblish et al. |
| 6,745,080 B2 | 6/2004 | Koblish |
| 6,917,834 B2 | 7/2005 | Koblish et al. |
| 7,175,619 B2 | 2/2007 | Koblish et al. |
| 7,186,250 B2 | 3/2007 | Koblish et al. |
| 7,435,248 B2 | 10/2008 | Taimisto et al. |
| 7,959,630 B2 | 6/2011 | Taimisto et al. |
| 2001/0020174 A1 | 9/2001 | Koblish |
| 2002/0004631 A1 | 1/2002 | Jenkins et al. |
| 2002/0087208 A1 | 7/2002 | Koblish et al. |

(Continued)

*Primary Examiner* — Michael Kahelin
*Assistant Examiner* — Mallika D Fairchild
(74) *Attorney, Agent, or Firm* — Seagate, Tufte & Wickhem, LLC

(57) ABSTRACT

Disclosed herein, among other things, are methods and apparatus related to radio frequency (RF) ablation catheters. The present subject matter provides a method for forming an ablation catheter having a balloon at a distal end of the catheter. The method includes applying a band of conductive material to an outer surface of the balloon. The band of conductive material is adapted to provide one or more electrodes for radio frequency ablation therapy. A distal end of a lead is connected to the band of conductive material. The balloon is inverted, so that the inverted balloon includes the band of conductive material on an inside surface. According to various embodiments, the balloon includes a semi-permeable or hydro-able membrane.

20 Claims, 5 Drawing Sheets

(56) References Cited

U.S. PATENT DOCUMENTS

| | | |
|---|---|---|
| 2003/0014049 A1 | 1/2003 | Koblish et al. |
| 2003/0153967 A1 | 8/2003 | Koblish et al. |
| 2003/0195406 A1 | 10/2003 | Jenkins et al. |
| 2004/0049182 A1 | 3/2004 | Koblish et al. |
| 2005/0015083 A1 | 1/2005 | Koblish et al. |
| 2005/0059965 A1* | 3/2005 | Eberl et al. .............. 606/41 |
| 2005/0070887 A1 | 3/2005 | Taimisto et al. |
| 2009/0018534 A1 | 1/2009 | Taimisto et al. |

* cited by examiner

INVERTED BALLOON RF ABLATION CATHETER AND METHOD

CLAIM OF PRIORITY

This application claims the benefit of priority under 35 U.S.C. §119(e) of Kim et al., U.S. Provisional Patent Application Ser. No. 61/416,597, entitled "INVERTED BALLOON RF ABLATION CATHETER AND METHOD", filed on Nov. 23, 2010, which is herein incorporated by reference in its entirety.

TECHNICAL FIELD

This application relates generally to medical devices and, more particularly, to systems and methods related to ablation catheters.

BACKGROUND

Aberrant conductive pathways disrupt the normal path of the heart's electrical impulses. For example, conduction blocks can cause the electrical impulse to degenerate into several circular wavelets that disrupt the normal activation of the atria or ventricles. The aberrant conductive pathways create abnormal, irregular, and sometimes life-threatening heart rhythms called arrhythmias. Ablation is one way of treating arrhythmias and restoring normal contraction. The sources of the aberrant pathways (called focal arrhythmia substrates) are located or mapped using mapping electrodes. After mapping, the physician may ablate the aberrant tissue. In radio frequency (RF) ablation, RF energy is directed from the ablation electrode through tissue to ablate the tissue and form a lesion.

SUMMARY

Disclosed herein, among other things, are methods and apparatus related to radio frequency (RF) ablation catheters. The present subject matter provides an ablation catheter system including a balloon disposed at a distal end of a catheter and a band of conductive material on an inside surface of the balloon. The band of conductive material is formed by application to an outer surface of the balloon before turning the balloon inside-out. The conductive material is adapted to provide one or more electrodes for radio frequency ablation therapy. A lead has a distal end connected to the band of conductive material and a proximal end connected to stimulation circuitry to provide ablation therapy to a lesion site proximal to the balloon. According to various embodiments, the balloon includes a semi-permeable or hydro-able membrane.

One aspect of the present subject matter includes a method for forming an ablation catheter having a balloon at a distal end of the catheter. The method includes applying a band of conductive material to an outer surface of the balloon. The band of conductive material is adapted to provide one or more electrodes for radio frequency ablation therapy. A distal end of a lead is connected to the band of conductive material. The balloon is inverted, so that the inverted balloon includes the band of conductive material on an inside surface.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an," "one," or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

When treating atrial fibrillation with RF ablation, it is desirable to obtain circumferential contact with lesion sites at the antrum or ostium of a pulmonary vein (PV). A therapeutic catheter using a balloon designed to mold around the lesion site is disclosed herein. A semi-permeable or hydro-able balloon membrane is incorporated in the described balloon ablation catheter, in various embodiments. In an embodiment, the catheter includes a single semi-compliant balloon in the distal end. The balloon incorporates a band or series of band patterns on its effective area, the band including a conductive, flowable material such as platinum, gold or silver. These band materials are used to conduct and transmit RF energy. After the application of the conductive material on to the effective area of the balloon exterior and corresponding connection of lead wires, the balloon is inverted, or turned inside-out, so that the effective area of conductive material now resides inside the balloon. This process allows for easy manufacturing as well as ensuring a safer ablation procedure. The permeable balloon, once hydrated with ionic fluid, creates a conductive path from the electrode material through the balloon to the tissue. Because the electrode is not in direct contact with the tissue, the current density is dispersed through the balloon material to create a more distributed conduction path. This reduces the likelihood of localized heating which could lead to thrombus, char/coagulum, etc. In addition, with the printed conductive material contained within the balloon, the likelihood of issues such as electrodes flaking off into the body or becoming oxidized to the point of changing electrode impedance will be minimized. Because the balloon includes a semi-permeable or hydro-able material, the RF energy from the conductive layer inside the balloon will be transmitted directly to the tissue treatment site.

Figure 1:
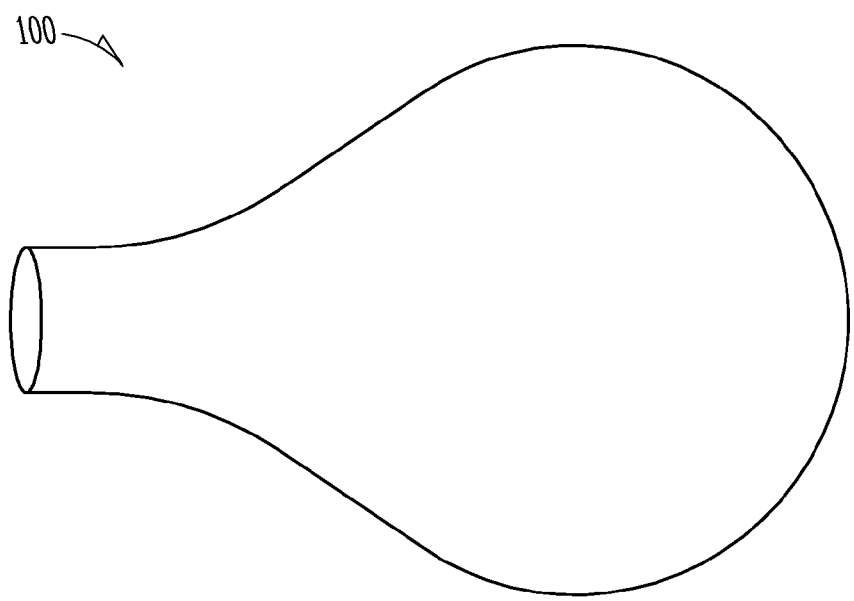
FIGS. 1-6 illustrate planar and cross-sectional views of an ablation balloon catheter system, according to various embodiments of the present subject matter.
Figure 2:
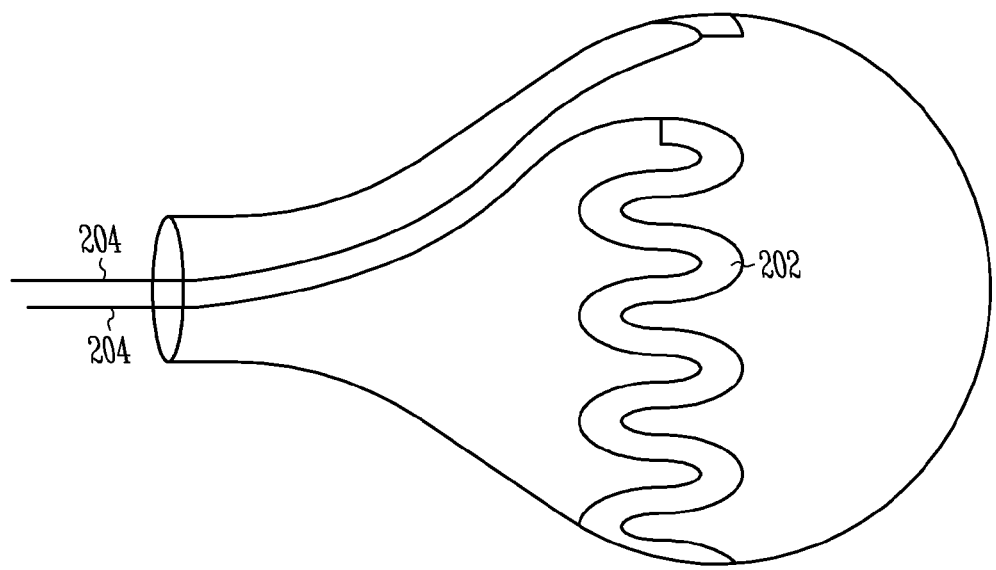
Figure 3:
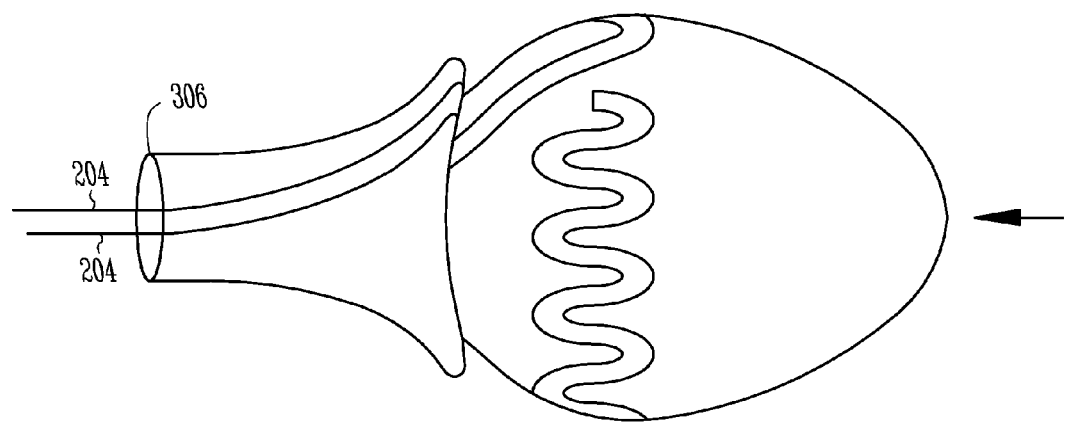
Figure 4:
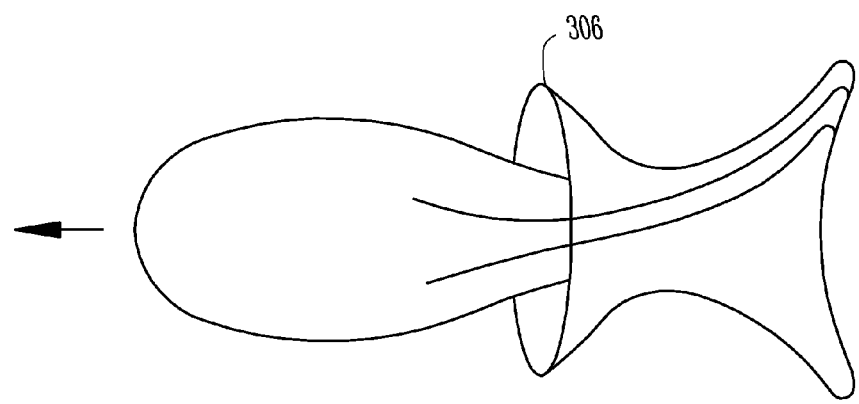
Figure 5:
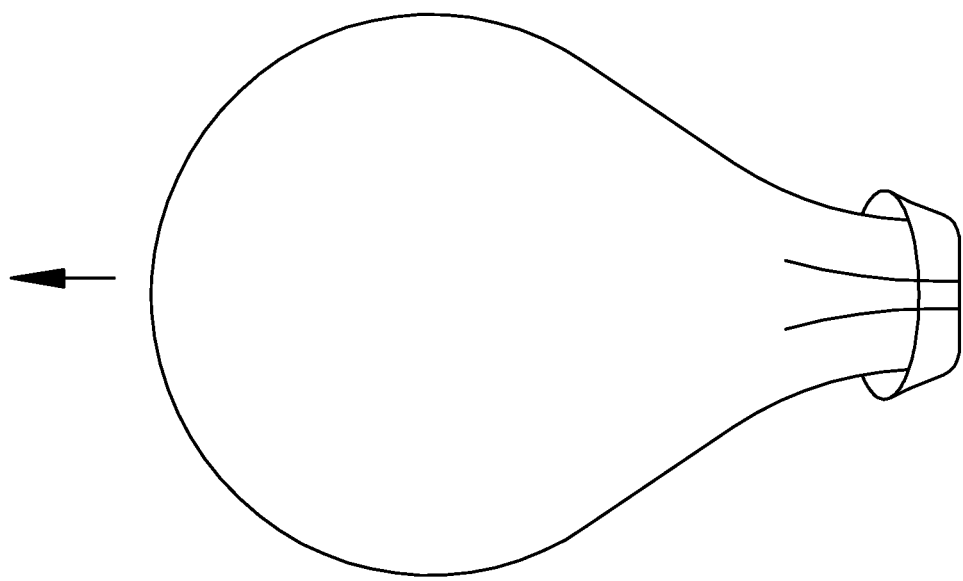
Figure 6:
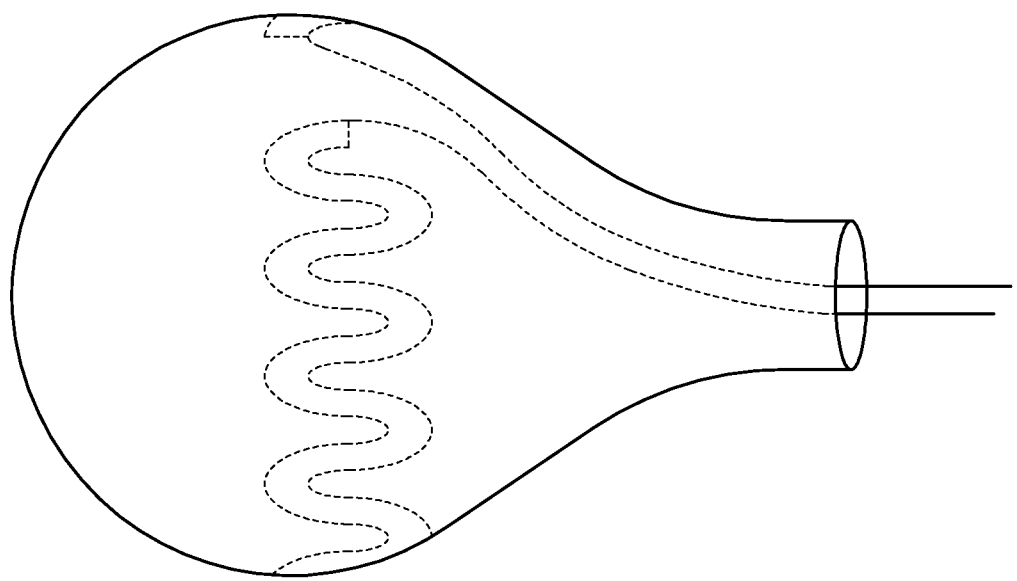

FIGS. 1-6 illustrate planar and cross-sectional views of an ablation balloon catheter system, according to various embodiments of the present subject matter. FIG. 1 illustrates a balloon 100 having a semi-permeable or hydro-able membrane for use in an ablation catheter system. In various embodiments, the semi-permeable material includes a polymer material, such as a urethane material, that has been processed to incorporate micro holes using laser or other technology. In one embodiment, the hydro-able material includes a material that provides for transmission of RF energy through the material to tissue via ionic transport. One example of hydro-able material includes a Tecophilic® material. FIG. 2 shows a conductive material 202 applied to the exterior of the balloon and connected to the distal end of at least one lead 204. The conductive material is printed on the balloon, in an embodiment. The conductive material is used to transmit RF energy, in various embodiments. In one embodiment, the conductive material is printed on the balloon using pad printing. In another embodiment, the conductive material is printed on the balloon using needle ink printing. In various embodiments, a silver pad or conductive layer of ink is used as the conductive material. FIGS. 3-5 show the balloon being inverted, or turned inside-out, according to various embodiments. In FIG. 3, a portion 306 of the balloon proximal the leads is rolled back to begin the inversion. FIG. 4 shows a partially inverted balloon, according to various embodiments. In FIG. 5, most of the balloon has been inverted. FIG. 6 shows the resulting balloon catheter having the conductive material and connections on the interior surface of the balloon.

The present subject matter provides an ablation catheter system including a balloon disposed at a distal end of a catheter and a band of conductive material on an inside surface of the balloon. The band of conductive material is formed by application to an outer surface of the balloon before turning the balloon inside-out. The conductive material is adapted to provide one or more electrodes for radio frequency ablation therapy. A lead has a distal end connected to the band of conductive material and a proximal end connected to stimulation circuitry to provide ablation therapy to a lesion site proximal to the balloon. According to various embodiments, the balloon includes a semi-permeable or hydro-able membrane. In one embodiment, the hydro-able membrane includes a Tecophilic® membrane. Tecophilic® material is urethane-based and has a high percentage of absorption. In another embodiment, the membrane includes a Pebax® membrane. The balloon is shaped to form around a pulmonary vein lesion site, in an embodiment. In various embodiments, the balloon is shaped to form a circumferential contact to an antrum or ostium of a pulmonary vein. In various embodiments, other balloon shapes are used to provide ablation to other portions of the human anatomy. According to various embodiments, the band of conductive material includes a flowable ink material. The band of conductive material includes platinum, gold and/or silver, in various embodiments. Other conductive materials can be used without departing from the scope of this disclosure. According to various embodiments, the flexibility of the balloon material is matched to the flexibility of the printed conductive material to prevent breakage of the conductive material when inverting or stretching the balloon. In one embodiment, the conductive material will accordion in and out when the balloon is stretched. The conductive material can be applied to a deflated balloon, an inflated balloon or a partially inflated balloon, in various embodiments.

Figure 7:
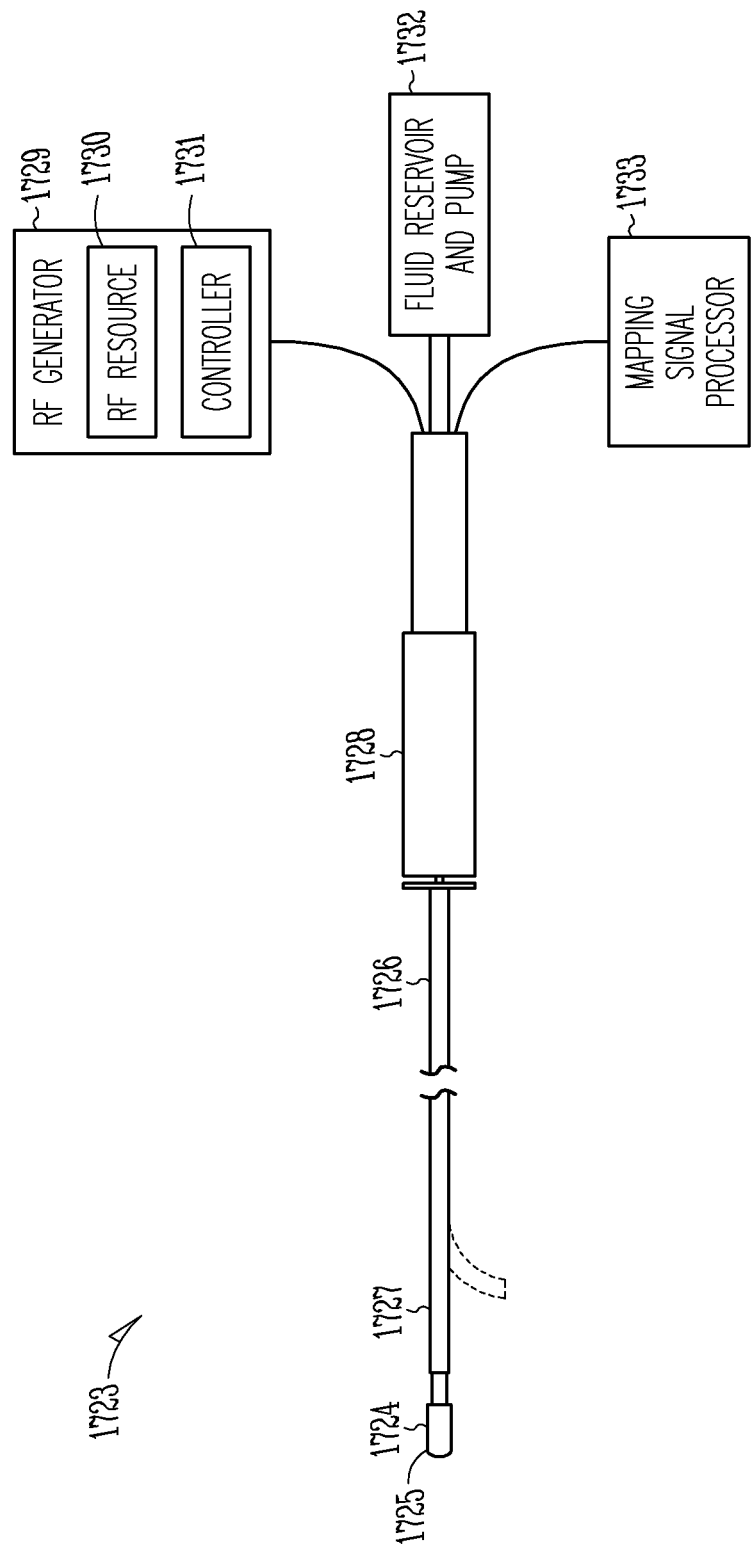
FIG. 7 illustrates a mapping and ablation system, according to various embodiments of the present subject matter.

FIG. 7 illustrates a mapping and ablation system 1723, according to various embodiments of the present subject matter. The illustrated system includes an open-irrigated catheter, but could be used with closed irrigation catheters or non-irrigation catheters. The illustrated catheter includes an ablation tip 1724 with an RF ablation electrode 1725 and irrigation ports therein. The catheter can be functionally divided into four regions: the operative distal ablation electrode 1725, a main catheter region 1726, a deflectable catheter region 1727, and a proximal catheter handle region where a handle assembly 1728 including a handle is attached. A body of the catheter includes a cooling fluid lumen and may include other tubular element(s) to provide the desired functionality to the catheter. The addition of metal in the form of a braided mesh layer sandwiched in between layers of plastic tubing may be used to increase the rotational stiffness of the catheter.

The deflectable catheter region 1727 allows the catheter to be steered through the vasculature of the patient and allows the probe assembly to be accurately placed adjacent the targeted tissue region. A steering wire (not shown) may be slidably disposed within the catheter body. The handle assembly may include a steering member to push and pull the steering wire. Pulling the steering wire causes the wire to move proximally relative to the catheter body which, in turn, tensions the steering wire, thus pulling and bending the catheter deflectable region into an arc. Pushing the steering wire causes the steering wire to move distally relative to the catheter body which, in turn, relaxes the steering wire, thus allowing the catheter to return toward its form. To assist in the deflection of the catheter, the deflectable catheter region may be made of a lower durometer plastic than the main catheter region.

The illustrated system 1723 includes an RF generator 1729 used to generate the power for the ablation procedure. The RF generator 1729 includes a source 1730 for the RF power and a controller 1731 for controlling the timing and the level of the RF power delivered through the ablation tip 1724. The illustrated system 1723 also includes a fluid reservoir and pump 1732 for pumping cooling fluid, such as a saline, through the catheter and out through the irrigation ports. Some system embodiments incorporate a mapping function. Mapping electrodes may be incorporated into the catheter system. In such systems, a mapping signal processor 1733 is connected to the mapping electrodes to detect electrical activity of the heart. This electrical activity is evaluated to analyze an arrhythmia and to determine where to deliver the ablation energy as a therapy for the arrhythmia. One of ordinary skill in the art will understand that the modules and other circuitry shown and described herein can be implemented using software, hardware, and/or firmware. Various disclosed methods may be implemented as a set of instructions contained on a computer-accessible medium capable of directing a processor to perform the respective method. The catheter includes a balloon at the distal end, such as the balloon of FIG. 6, in various embodiments.

Figure 8:
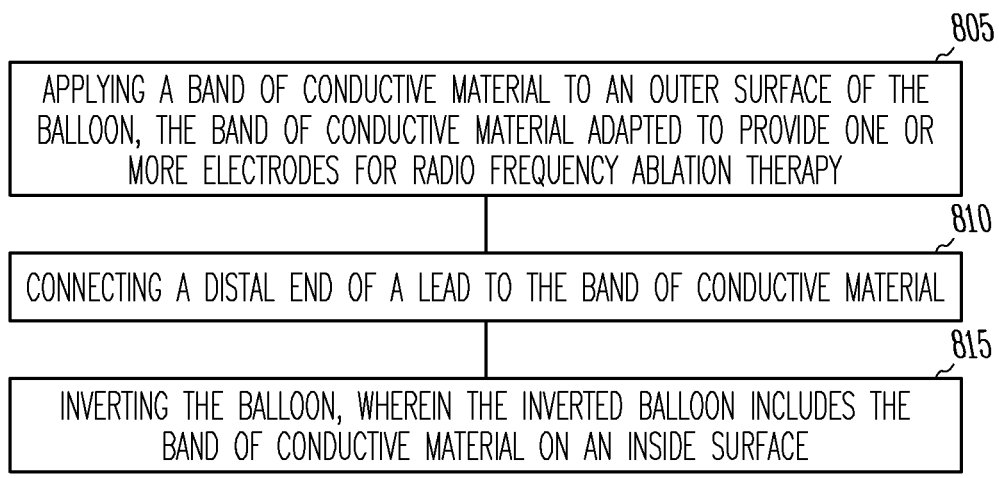
FIG. 8 illustrates a flow diagram of a method for forming an ablation catheter having a balloon at a distal end of the catheter, according to an embodiment of the present subject matter.

FIG. 8 illustrates a flow diagram of a method for forming an ablation catheter having a balloon at a distal end of the catheter, according to an embodiment of the present subject matter. The method includes applying a band of conductive material to an outer surface of the balloon, at 805. The band of conductive material is adapted to provide one or more electrodes for radio frequency ablation therapy. A distal end of a lead is connected to the band of conductive material, at 810. At 815, the balloon is inverted, so that the inverted balloon includes the band of conductive material on an inside surface.

According to various embodiments, applying the band of conductive material includes printing the band of conductive material on the outer surface of the balloon. The balloon includes a semi-permeable or hydro-able membrane, in various embodiments. The method further includes placing the balloon in circumferential contact with a pulmonary vein, in an embodiment. In one embodiment, the method also includes hydrating the balloon to create a conductive path from the conductive material through the balloon to adjacent tissue, and applying radio frequency stimulation through the balloon to the adjacent tissue to perform ablation using the band of conductive material. In one embodiment, hydrating the balloon includes applying an ionic fluid to the balloon. In another embodiment, hydrating the balloon includes placing the balloon in contact with blood. The balloon is placed in contact with an antrum or ostium of the pulmonary vein, in various embodiments One of ordinary skill in the art will understand that, the modules and other circuitry shown and described herein can be implemented using software, hardware, and/or firmware. Various disclosed methods may be implemented as a set of instructions contained on a computer-accessible medium capable of directing a processor to perform the respective method.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. A method for forming an ablation catheter having a balloon at a distal end of the catheter, the method comprising:
    applying a band of conductive material to an outer surface of the balloon, the band of conductive material adapted to provide one or more electrodes for radio frequency ablation therapy;
    connecting a distal end of a lead to the band of conductive material; and
    inverting the balloon, wherein the inverted balloon includes the band of conductive material on an inside surface.

2. The method of claim 1, wherein applying the band of conductive material includes printing the band of conductive material on the outer surface of the balloon.

3. The method of claim 1, wherein inverting the balloon includes inverting a balloon having a semi-permeable membrane.

4. The method of claim 1, wherein inverting the balloon includes inverting a balloon having a hydro-able membrane.

5. The method of claim 4, further comprising:
    placing the balloon in circumferential contact with a pulmonary vein.

6. The method of claim 5, further comprising:
    hydrating the balloon to create a conductive path from the conductive material through the balloon to adjacent tissue.

7. The method of claim 6, further comprising:
    applying radio frequency stimulation through the balloon to the adjacent tissue to perform ablation using the band of conductive material.

8. The method of claim 6, wherein hydrating the balloon includes applying an ionic fluid to the balloon.

9. The method of claim 8, wherein hydrating the balloon includes placing the balloon in contact with blood.

10. The method of claim 5, wherein placing the balloon in circumferential contact with the pulmonary vein includes placing the balloon in contact with an antrum or ostium of the pulmonary vein.

11. A method for forming an ablation catheter having a balloon at a distal end of the catheter, the method comprising:
    applying a pattern of conductive material on an outer surface of the balloon, the pattern of conductive material having a flexibility matching that of the balloon, the conductive material adapted to provide one or more electrodes for radio frequency ablation therapy;
    connecting a distal end of at least one lead to the pattern of conductive material; and
    inverting the balloon, wherein the inverted balloon includes the pattern of conductive material on an inside surface.

12. The method of claim 11, wherein the at least one lead includes two or more leads.

13. The method of claim 11, wherein applying the pattern of conductive material includes applying the conductive material onto the balloon in a deflated state.

14. The method of claim 11, wherein applying the pattern of conductive material includes applying the conductive material onto the balloon in a partially inflated state.

15. The method of claim 11, wherein applying the pattern of conductive material includes applying a discontinuous pattern of conductive material onto the outer surface of the balloon.

16. The method of claim 11, wherein inverting the balloon includes inverting a balloon having a hydro-able membrane.

17. The method of claim 16, further comprising:
    placing the balloon in circumferential contact with a pulmonary vein; and
    hydrating the balloon to create a conductive path from the conductive material through the balloon to adjacent tissue.

18. The method of claim 17, further comprising:
    applying radio frequency stimulation through the balloon to the adjacent tissue to perform ablation using the pattern of conductive material.

19. The method of claim 17, wherein hydrating the balloon includes applying an ionic fluid to the balloon.

20. The method of claim 17, wherein placing the balloon in circumferential contact with the pulmonary vein includes placing the balloon in contact with an antrum or ostium of the pulmonary vein.

* * * * *